United States Patent [19]

Geen et al.

[11] Patent Number: 5,886,215

[45] Date of Patent: *Mar. 23, 1999

[54] 2-ACETOXYMETHYL-4-HALO-BUTYL-1-YL ACETATES

[75] Inventors: Graham Richard Geen, Stansted Mountfichet; Richard Lewis Jarvest, Surbiton, both of England

[73] Assignee: SmithKline Beecham plc, Brentford, England

[*] Notice: This patent issued on a continued prosecution application filed under 37 CFR 1.53(d), and is subject to the twenty year patent term provisions of 35 U.S.C. 154(a)(2).

[21] Appl. No.: 884,731

[22] Filed: Jun. 30, 1997

Related U.S. Application Data

[62] Division of Ser. No. 258,167, Jun. 10, 1994, Pat. No. 5,684,153, which is a continuation of Ser. No. 132,082, Oct. 5, 1993, abandoned, which is a continuation of Ser. No. 825,440, Jan. 22, 1992, Pat. No. 5,250,688, which is a continuation of Ser. No. 285,399, Dec. 15, 1988, abandoned, which is a continuation of Ser. No. 777,188, Sep. 18, 1985, abandoned, and a continuation-in-part of Ser. No. 918,111, Jul. 20, 1992, abandoned, which is a continuation of Ser. No. 607,403, Oct. 31, 1990, abandoned, which is a continuation of Ser. No. 85,216, Aug. 12, 1987, Pat. No. 5,075,455, which is a continuation of Ser. No. 641,300, Aug. 16, 1984, abandoned.

[30] Foreign Application Priority Data

| Aug. 18, 1983 | [GB] | United Kingdom | 8322199 |
| Sep. 21, 1983 | [GB] | United Kingdom | 8325271 |
| Sep. 20, 1984 | [GB] | United Kingdom | 8423833 |
| Apr. 23, 1985 | [GB] | United Kingdom | 8510331 |
| Aug. 16, 1985 | [GB] | United Kingdom | 8520618 |

[51] Int. Cl.⁶ ................................................. C07C 67/02
[52] U.S. Cl. ........................................................ 560/264
[58] Field of Search ............................................. 560/264

[56] References Cited

U.S. PATENT DOCUMENTS

| 4,146,715 | 3/1979 | Schaeffer | 544/276 |
| 4,451,478 | 5/1984 | Simon et al. | |
| 4,461,757 | 7/1984 | Ogilvie | 424/85 |
| 4,495,190 | 1/1985 | Hagberg et al. | 514/262 |
| 4,579,849 | 4/1986 | MacCoss et al. | 514/262 |
| 4,609,662 | 9/1986 | Krenitsky | 544/277 |
| 4,798,833 | 1/1989 | Johansson et al. | 544/277 |
| 4,845,084 | 7/1989 | Hannah et al. | 514/81 |

FOREIGN PATENT DOCUMENTS

| 0 055 239 | 6/1982 | European Pat. Off. |
| 0141927 | 5/1985 | European Pat. Off. |
| 0 152 316 | 8/1985 | European Pat. Off. |
| 0 186 640 | 7/1986 | European Pat. Off. |
| 352953 | 1/1990 | European Pat. Off. |
| 355986 | 2/1990 | European Pat. Off. |
| 369583 | 5/1990 | European Pat. Off. |
| 404296 | 12/1990 | European Pat. Off. |
| 1 523 865 | 9/1978 | United Kingdom |
| 2 104 070 | 3/1983 | United Kingdom |
| 2 122 197 | 1/1984 | United Kingdom |
| 2 122 198 | 1/1984 | United Kingdom |
| 2 130 204 | 5/1984 | United Kingdom |
| 2 151 622 | 7/1985 | United Kingdom |
| WO 93/23401 | 11/1993 | WIPO |

OTHER PUBLICATIONS

Gillen, Synthesis and properties of Novel Nucleoside and Nucleotide Analogues, PhD. Thesis (Apr. 19, 1980).

Pandit et al., Synthetic Communication, 2(6) 345–351 (1972).

Keller et al., Biochem. Pharm. 30 (22) 3071–3077 (1981).

Ericson et al., Antimicrobial Agents and Chemotherapy, 27(5), 753–759 (1985).

Ashton et al., J. Med Chem., 28, 926–933 (1985).

Oberg et al., J. Antimicrob. Chemother., 14 (Suppl A), 5–26 (1984).

Grose, PhD. Thesis, Synthesis of Nucleoside Analogues, Univ. of Amersterdam (1971).

Stewart et al., "The Peptides", vol. 3, pp. 172, 180, 181 (1981).

Tippie, et al., Nucleosides & Nucleotide, 3(5), 525–535 (1984).

Smith et al., Antimicrob. Agents Chemotherapy, vol. 22, No. 1, pp. 55–61 (Jul. 1982).

Martin et al., J. Med. Chem., vol. 22, pp. 759–761 (1983).

McGee et al., J. Med Chem., vol. 28, pp. 1242–1245 (1985).

Harnden et al., J. Chem Soc. Perkin Trans., I, pp. 2207–2213 (1989).

*Primary Examiner*—Gary Geist
*Assistant Examiner*—Rosalynd Keys
*Attorney, Agent, or Firm*—Dara L. Dinner; Stephen Venetianer

[57] ABSTRACT

The present invention provides a process for the synthesis of penciclovir and famciclovir by 9-substituting 2-amino-6-chloropurine (ACP) with an appropriate side chain precursor, followed by conversion of the 6-chloro moiety to a hydroxy moiety (i.e. to form a guanine) or hydrogen (to form a 2-aminopurine), respectively; and 2-acetoxymethyl-4-halo-butyl-1-yl acetates.

3 Claims, No Drawings

2-ACETOXYMETHYL-4-HALO-BUTYL-1-YL ACETATES

This is a Divisional of application Ser. No. 08/258,167, filed Jun. 10, 1994, ( U.S. Pat. No. 5,684,153) which is a Continuation of 08/132,082, filed Oct. 5, 1993 (abandoned), which is a Continuation of 07/825,440, filed Jan. 22, 1992 (U.S. Pat. No. 5,250,688), which is a Continuation of 07/285,399, filed Dec. 15, 1988, (abandoned) which is a Continuation of 06/777,188, filed Sep. 18, 1985, (abandoned) and Continuation-in-Part of 07/918,111, filed Jul. 20, 1992, (abandoned) which is a Continuation of 07/607,403, filed Oct. 31, 1990, (abandoned) which is a Continuation of 07/085,216, filed Aug. 12, 1987 (U.S. Pat. No. 5,075,455), which is a Continuation of 06/641,300, (abandoned) filed Aug. 16, 1984.

U.S. Pat. Nos. 5075445 and 5246937, the subject matter of which is incorporated herein by reference, disclose antiviral compounds penciclovir (Example 4 of '445) and famciclovir (Example 2 of '937) and methods for their preparation. 2-Amino-6-chloropurine (ACP) is 9-substituted with an appropriate side chain precursor, followed by conversion of the 6-chloro moiety to a hydroxy moiety (i.e. to form a guanine) or hydrogen (a 2-aminopurine).

In particular, beginning column 4 of '445, and column 3 of '937, a process is described for the preparation of such purine derivatives wherein the hydroxy groups in the 9-(4-hydroxy-3-hydroxymethylbut-1-yl) substituent are in acylated form, i.e. the ACP is reacted with 2-acyloxymethy-4-(leaving group)-but-1-yl acylate. The leaving group may be halo, such as chloro, bromo or iodo although alternative leaving groups, such as tosylate or methanesulphonate may be employed. The acyl groups have advantages over the alternative protecting groups already described in acyclonucleoside chemistry in providing a good yield of 9-substitution and avoiding by-products which are difficult to isolate.

The following examples illustrate the process of the invention to form 9-(4-acetoxy-3-acetoxymethylbut-1-yl)-2-amino-6-chloropurine, (DACP). The following descriptions illustrate the preparation of side chain intermediates. Penciclovir is prepared from DACP according to the method described in '445 column 14, lines 4–16 and famciclovir is prepared from DACP according to the method described in Example 2 of '937.

Example 1

2-Acetoxymethyl-4-bromobutyl acetate was reacted with ACP as described in Examples 11 and 10 of '445.

Example 2

A mixture of ACP (10.0 mmol), 2-acetoxymethyl-4-iodobutyl acetate (3.30 g, 10.5 mmol), and anhydrous potassium carbonate (2.07 g, 15.0 mmol) was stirred for 18 hours at ambient temperature in dry DMF (40 ml) under an atmosphere of dry nitrogen. The mixture was then filtered to remove insoluble material, which was washed well with DMF. The combined filtrates were evaporated under reduced pressure and the residue purified directly by column chromatography on silica gel (150 g), eluting with various dichloromethane-methanol mixtures. Fractions containing the first-eluting N-9 isomer, and the second-eluting N-7 isomer were separately combined, rigorously evaporated and weighed. The N-9:N-7 alkylated product ratio obtained from the isolated weights was checked by integration of the respective H-8 $^1$HNMR signals in the spectrum of the crude residue.

9- (4-Acetoxy-3-acetoxymethylbut)-2-amino-6-chloropurine and 7-(4-acetoxy-3-acetoxymethylbut)-2-amino-6-chloropurine Column eluant dichloromethane-methanol 25:1. 9-isomer, 75%, m.p. 134°–136° (ethyl acetate-diethyl ether).
$^1$HNMR: 1.80–2.05 (m 3H,CHCH$_2$), 2.00 (s,6H,2× COCH$_3$), 4.03 (d,4H,2×CH$_2$O), 4.15 (t,2H, CH$_2$N), 6.87 (brs, 2H,NH$_2$), 8.16 (s,1H, H-8). $^{13}$CNMR: 20.47 (2×CH$_3$), 27.75 (CH$_2$), 34.45 (CH), 40.88 (CH$_2$N), 63.43 (2×CH$_2$O), 123.43 (C-5), 143.07 (C-8), 149.34 (C-6), 154.02 (C-4), 159.68 (C-2), 170.27 (2×CO). U.V. $\lambda_{max}$ 223.5 ($\epsilon$27.600), 248.5 (5,800), 310 (7,700). Found; C: 47.14, H: 4.97, N: 19.69. C$_{14}$H$_{18}$N$_5$O$_4$Cl requires; C: 47.26, H: 5.10, N: 19.68%. 7-isomer, 15%, m.p. 159°–161° (dec). (butanol).
$^1$HNMR: 1.60–2.10 (m, 3H, CHCH$_2$), 2.00 (s, 6H, 2×COCH$_3$), 4.00 (d, 4H, 2×CH$_2$O), 4.34 (m, 2H, CH$_2$N), 6.56 (brs, 2H, NH$_2$), 8.33 (s, 1H, H-8). $^{13}$CNMR: 20.41 (2×CH$_3$), 29.80 (CH$_2$), 34.51 (CH), 44.06 (CH$_2$N), 63.46 (2×CH$_2$O), 114.65 (C-5), 141.97 (C-6), 149.28 (C-8), 159.81 (C-2), 164.24 (C-4), 170.12 (2×CO). U.V. $\lambda_{max}$ 222.5 ($\epsilon$23.600), 253.5sh (3,700), 323 (5,400) Found; C: 47.31, H: 5.17, N: 19.88. C$_{14}$H$_{18}$N$_5$O$_4$Cl requires; C: 47.26, H: 5.10, N: 19.68%.

2-Acetoxymetlyl-4-bromobutyl acetate was prepared as described in Examples 5–8 of '445.

2-Acetoxymetlyl-4-iodobutyl acetate was prepared as follows a) To a stirred solution of 2-(2-benzyloxyethyl)propane-1,3-diol (J. Org. Chem., 1981, 46, 3204) (10.5 g, 47.6 mmol), 4-dimethylaminopyridine (0.55 g, 4.5 mmol), and pyridine (12.3 ml 0.15 mol) in dichloromethane (54 ml) at −10° C. was added dropwise acetic anhydride(13.2 ml 0.14 mol) over 20 minutes. After completion of the addition, the reaction mixture was stirred for a further 1 hour at 0° C., then diluted with dichloromethane (100 ml) and washed with 2M hydrochloric acid (2×50 ml), saturated sodium bicarbonate solution (50 ml), and brine (50 ml), dried (MgSO$_4$), and evaporated to give 2-acetoxymethyl-4-benzyloxybutyl acetate as a light yellow oil (13.2 g, 94%). b.p. 160°–165° /0.5 mm.
$^1$HNMR: 1.62 (q,2H,CHC$\underline{H}_2$), 2.00 (s,6H,2×CH$_3$), 2.15 (m,1H,CH), 3.51 (t,2H,CH$_2$C$\underline{H}_2$O), 4.03 (m,4H,2×CH$_2$O), 4.46 (s,2H,OC$\underline{H}_2$Ph), 7.33 (m,5H,Ph).
$^{13}$CNMR: 20.31 (2×CH$_3$), 27.93 (CHC$\underline{H}_2$), 34.40 (CH), 63.73 (2×CH$_2$O), 67.22 (CH$_2$C$\underline{H}_2$O), 71.99 (C$\underline{H}_2$Ph), 127.22, 127.30, 128.09, 138.54 (Ph), 170.13 (2×CO). Found; C: 65.07, H: 7.76. C$_{16}$H$_{22}$O$_5$ requires; C: 65.29, H: 7.53%.

b) A solution of 2-acetoxymethyl-4-benzyloxybutyl acetate (15.5 g, 52.7 mmol) in ethanol (200 ml) was hydrogenated for 18 hours at ambient temperature over 10% palladium-carbon (2 g). Filtration and evaporation afforded the corresponding alcohol (10.2 g) as a colourless oil.

c) To a stirred solution of the above oil and triethylamine (10.4 ml, 74.8 mmol) in dichloromethane (100 ml) cooled to −5° C. was added a solution of methanesulphonyl chloride (4.6 ml, 59.5 mmol) in dichloromethane (30 ml) dropwise over 30 minutes. After completion of the addition, the reaction mixture was stirred for a further 1 hour at −5° C., then washed with 2M hydrochloric acid (2×100 ml), saturated sodium bicarbonate solution (100 ml), and brine (100 ml), dried (MgSO$_4$) and evaporated to afford the corresponding methanesulphonate (14.1 g) as a pale yellow oil.

d) A mixture of the above oil and sodium iodide (15.0 g, 0.1 mol) was stirred under reflux for 2 hours in acetone (150 ml), then cooled, poured into water (300 ml), and extracted with diethyl ether (3×150 ml). The combined ether extracts were washed with 10% sodium metabisulphite solution (250 ml), and brine (250 ml), dried (MgSO$_4$) and evaporated to give a pale oil. This was purified by flash column chromatography on silica, eluant hexane-diethyl ether 3:2 affording the title compound as a colourless oil (13.1 g, 79% from 2-acetoxymethyl-4-benzyloxybutyl acetate).

$^1$HNMR: 1.88 (q,2H,CH$_2$), 2.02 (s,6H,2×CH$_3$), 2.10 (m,1H,CH), 3.33 (t,2H,CH$_2$I), 4.02 (d,4H,2×CH$_2$O).

$^{13}$CNMR: 5.01 (CH$_2$I), 20.48 (2×CH$_3$), 32.04 (CH$_2$), 37.87 (CH), 62.86 (2×CH$_2$O), 170.02 (2×CO).

EI-MS. m/e: 314 (M$^+$), 254 (M$^+$-HOAc), 211 (M$^+$-HOAcAc), 187 (M$^+$-I). Found; C: 34.56, H: 4.99. C$_9$H$_{15}$O$_4$I requires; C: 34.42, H: 4.81%.

We claim:

1. A compound known as 2-acetoxymethyl-4-halo-but-1-yl acetate.

2. A compound according to claim 1 wherein halo is bromo.

3. A compound according to claim 1 wherein halo is iodo.

* * * * *